United States Patent
Watts et al.

(10) Patent No.: US 9,393,142 B2
(45) Date of Patent: Jul. 19, 2016

(54) FORESKIN STRETCHING

(75) Inventors: Alan Watts, Chatswood (AU); Andrew E. James, Castle Cove (AU)

(73) Assignee: IPH001 PTY LTD, New South Wales (AU)

( * ) Notice: Subject to any disclaimer, the term of this patent is extended or adjusted under 35 U.S.C. 154(b) by 1223 days.

(21) Appl. No.: 12/991,816

(22) PCT Filed: May 8, 2009

(86) PCT No.: PCT/AU2009/000576
§ 371 (c)(1),
(2), (4) Date: Mar. 24, 2011

(87) PCT Pub. No.: WO2009/135268
PCT Pub. Date: Nov. 12, 2009

(65) Prior Publication Data
US 2011/0166414 A1    Jul. 7, 2011

(30) Foreign Application Priority Data
May 9, 2008  (AU) ................................ 2008902281

(51) Int. Cl.
*A61F 5/00* (2006.01)
(52) U.S. Cl.
CPC ...................................... *A61F 5/00* (2013.01)
(58) Field of Classification Search
CPC ........... A61B 2019/302; A61B 17/326; A61B 17/32056; A61B 19/24; A61F 5/41
USPC ................................ 600/38–41; 128/897, 898
See application file for complete search history.

(56) References Cited

U.S. PATENT DOCUMENTS

| | | | | |
|---|---|---|---|---|
| 157,343 A | * | 12/1874 | Molesworth | 606/192 |
| 2,161,274 A | * | 6/1939 | Behrend | 446/224 |
| 2,412,597 A | * | 12/1946 | Brewer | 251/181 |
| 2,589,985 A | * | 3/1952 | Borneman | 251/181 |
| 3,475,002 A | | 10/1969 | Phillips | |
| 3,999,538 A | * | 12/1976 | Philpot, Jr. | 600/370 |
| 6,139,515 A | | 10/2000 | Ito | |
| 6,880,808 B2 | * | 4/2005 | McPeak et al. | 251/309 |
| 2004/0098003 A1 | | 5/2004 | Nishiki | |

FOREIGN PATENT DOCUMENTS

| | | |
|---|---|---|
| DE | 199 25 156 C1 | 8/2000 |
| EP | 0 610 099 A2 | 8/1994 |
| WO | 90/04431 A1 | 5/1990 |

(Continued)

OTHER PUBLICATIONS

Definition printed from internet Aug. 9, 2014, "elongate", 1 page.*

(Continued)

*Primary Examiner* — Samuel Gilbert
(74) *Attorney, Agent, or Firm* — McDermott Will & Emery LLP

(57) ABSTRACT

A device (10) for stretching the foreskin of a subject is disclosed. The device has a body (10) having a passage (14) that extends through the body (10) to a distal end (18). The distal end (18) is adapted to receive a balloon (B). Fluid may be introduced through the passage (14) to cause the balloon (B) to expand. A flow regulating member (20) is positioned across the passage (14) to selectively close the passage (14) to fluid flow.

8 Claims, 3 Drawing Sheets

(56) References Cited

FOREIGN PATENT DOCUMENTS

WO 95/32011 A1 11/1995
WO 2004/047616 A2 6/2004

OTHER PUBLICATIONS

Hey, Zhou XH, "Balloon Dilation Treatment of Phimosis in Boys", Chinese Medical Journal 104(b) pp. 491-493, 1991.

Platigo Corporation. How does it work? Jan. 16, 2008 retrieved on Jun. 9, 2009 from http://gfs.platigo.com/how-does-it-work.html.

Platigo Corporation. About the GFS Kit May 3, 2007 retrieved on Jun. 9, 2009 from http://gfs.platigo.com/gfs_kit.html.

Supplementary European Search Report, dated Aug. 24, 2015 in Application No. 09 741 597.0.

* cited by examiner

FORESKIN STRETCHING

RELATED APPLICATIONS

This application is the U.S. National Phase under 35 U.S.C. §371 of International Application No. PCT/AU2009/000576, filed on May 8, 2009, which in turn claims the benefit of Australia Application No. 2008902281, filed on May 9, 2008, the disclosures of which Applications are incorporated by reference herein.

TECHNICAL FIELD

A device is disclosed for stretching the foreskin of a male subject.

BACKGROUND ART

Phimosis is a condition in which the male foreskin is unable to retract properly from the head of the penis (or glans) due to an unusually tight foreskin. Many males with the condition are born with it. Over time phimosis can also be exacerbated by tearing of the opening of the foreskin, resulting in scarring. Phimosis can result in a higher likelihood of infection, a build-up of smeg (the white substance under the foreskin), ballooning of the foreskin during urination, pain during sex and a loss of sensation during sex. A more serious condition, paraphimosis, occurs when a tight foreskin is pulled back over the head of the penis and remains there, constricting the blood flow. This can rapidly lead to permanent damage and/or loss of the penis.

US2004098003 discloses a device for stretching the foreskin that comprises a metal caliper. Tips of the caliper are inserted into the opening in the foreskin and then handles of the device are squeezed to urge the tips apart, so that the foreskin is gradually stretched until it can be properly retracted. The device can cause serious damage if not used correctly.

Another device comprises a plastic tube through which a balloon is inserted and held in place using a rubber grommet, the tube and grommet being held together with an O-ring. The balloon is inserted into the opening in the foreskin and then inflated. At a desirable level of inflation, the balloon is twisted and held with a balloon clip to prevent air leaking. However, the clip can cause damage to the balloon resulting in it bursting. In addition, the O-ring and grommet can come apart under pressure from the plastic.

It is to be understood that, for prior art information referred to herein, such reference does not constitute an admission that the information forms a part of the common general knowledge of a person of ordinary skill in the art, in Australia or any other country.

SUMMARY OF THE DISCLOSURE

In a first aspect there is disclosed a device for use in stretching the foreskin of a subject, the device comprising:
a body having a passage that extends therethrough to a distal end, the body being adapted at the distal end for receiving a balloon thereat whereby a fluid introduced through the passage can cause the balloon to expand; and
a fluid flow regulating member positionable across the passage to selectively close the passage to fluid flow.

The employment of a fluid flow regulating member that can be positioned across the passage enables the balloon expansion to be maintained without requiring balloon twisting or a balloon clip. This makes the device easy to use and also preserves balloon life. The employment of just a body and a flow regulating member also allows the device to be formed easily and be made robust, and to be easy to use.

The term "subject" typically refers to a human male, though the device could be adapted for use with other mammals having a foreskin.

In one form the fluid flow regulating member can be a tap that extends through at least part of the body and transversely across the passage. The tap can be rotatable about a lengthwise axis to respectively open or close the passage to fluid flow. Whilst a tap is a simple means of providing fluid flow regulation, other means may include a controllable (eg. switchable) valve locatable in the body, a slidable passage gate etc.

In one embodiment the tap can have a passage extending transversely therethrough. The tap passage can be of around the same diameter as the body passage, and can be selectively alignable with the body passage by the rotation of the tap. Thus, when the tap and body passages are aligned fluid can flow through the body via these passages. However, when the tap and body passages are progressively misaligned (ie. by rotation of the tap) such fluid flow via these passages is progressively restricted and ultimately prevented. Prevention of fluid flow (ie. closing of the passage through the body) can occur quite quickly, however, in some cases a restricted fluid flow may be desired to provide subtle adjustments to balloon expansion/contraction.

In one embodiment the tap can have a shank that is received snugly within an aperture that extends transversely through the body to intersect with the body passage. The tap passage can then extend transversely through the shank at a location such that, when the tap is snugly received in the aperture, the tap passage can be aligned with the body passage.

In one embodiment the tap can further comprise a manually graspable head located at the shank end, the head being located outside the aperture when the tap is snugly received therein.

In one form the body is elongate. In this form the passage can extend from a proximal end of the body that opposes the distal end. Then, at the proximal end, the passage can be sized to snugly receive therein the nozzle of a standard syringe, such as a luer syringe. This can make for easy expansion (eg. inflation) and contraction (eg. deflation) of the balloon.

In one embodiment the body distal end can be shaped to receive a balloon neck thereover (ie. to make for easy balloon mounting to the device). The body distal end may also comprise at least one circumferential groove adapted for receiving an O-ring therein. Such an O-ring can be used to easily and readily fasten the balloon neck at the body distal end. Also, two such grooves can be provided, for receiving two O-rings for additional security of mounting; or one groove for receiving therein a peripheral rib of the balloon neck end, and the other groove for the O-ring.

In one embodiment the body steps down in size at the distal end to define a spigot at that end, over which the balloon neck can be received. Again, this can make for easy balloon mounting to the device.

In one embodiment the body distal end is shaped to receive a balloon connector. The balloon connector has a distal end shaped to receive a balloon neck and a proximal end shaped to connect to the body distal end. In one form the proximal end of the balloon connector is adapted to fit snugly into the passage at the distal end of the body of the device. The balloon connector allows different balloons to be used with the same device or replacement balloons to be connected to the device if the original balloons break or wear down with time.

In one form the body can be formed of a relatively softer material (eg. a soft polymer, such as a rubber or silicon material) than the fluid flow regulating member (which can be formed of eg. a harder/rigid plastic material). This can enable the device to provide improved sealing of: a) the balloon at one end of the body and b) a fitting (eg. for a luer syringe) at other end of the body. This can also ensure a good, snug seal around the fluid flow regulating member passage to prevent fluid leakage.

In a second aspect there is disclosed a method for stretching the foreskin of a subject, the method comprising the steps of:
(i) locating a balloon at the distal end of the body of the device as defined the first aspect;
(ii) locating the balloon wholly or partly within the foreskin;
(iii) actuating the fluid flow regulating member to open the body passage to fluid flow;
(iv) introducing a fluid through the passage and into the balloon to cause it to expand;
(v) whilst maintaining the balloon in its expanded state, actuating the fluid flow regulating member to close the body passage to fluid flow.

It should be noted in the method that the fluid flow regulating member can, prior to locating the balloon at the body distal end, already be actuated to open the body passage to fluid flow. Thus, step (iii) could occur before step (i), or between steps (i) and (ii).

In step (ii) of the method location of the balloon can be assisted by a location rod inserted through the device and into the balloon, the rod assisting with balloon manipulation within the foreskin.

In step (v) of the method the balloon can be maintained in its expanded state within the foreskin for a period of time that is determined to be optimal for maintaining after use a semi-permanent or permanent foreskin stretch, for example, around 3-5 minutes.

In one embodiment step i) to v) are repeated daily for several consecutive days. Steps i) to v) may be repeated daily for 14 consecutive days. Steps i) to v) may be repeated twice daily for 14 consecutive days. In some forms of the method steps i) to v) may be repeated daily or twice daily for 28 consecutive days. In some form steps i) to v) may need to be repeated for longer than 28 consecutive days, for example 36 days.

In the method the balloon can be secured on the body distal end by locating at least one O-ring to extend around and clamp a neck of the balloon onto the body distal end.

In the method the balloon can optimally be inflated by a gas such as air, in which case the balloon can be inflated/deflated. However, in some applications a fluid in the form of a liquid such as water may be employed to expand the balloon (eg. warm water in winter months).

In the method the gas can be injected out of a syringe that has been inserted into the proximal end of the passage, such as a luer syringe.

The method may be employed in conjunction with the use of a topical steroid cream which is applied to the foreskin prior to using the device. The topical steroid cream may be any topical steroid cream suitable for making the skin of the foreskin amendable to stretching. For example, the topical steroid cream may contain 0.05% betamethasone.

BRIEF DESCRIPTION OF THE DRAWINGS

Notwithstanding any other embodiments which may incorporate some or all of the features as outlined in the Summary, specific device and method embodiments will now be described, by way of example only, with reference to the accompanying drawings in which.

DETAILED DESCRIPTION OF SPECIFIC EMBODIMENTS

Figure 1:
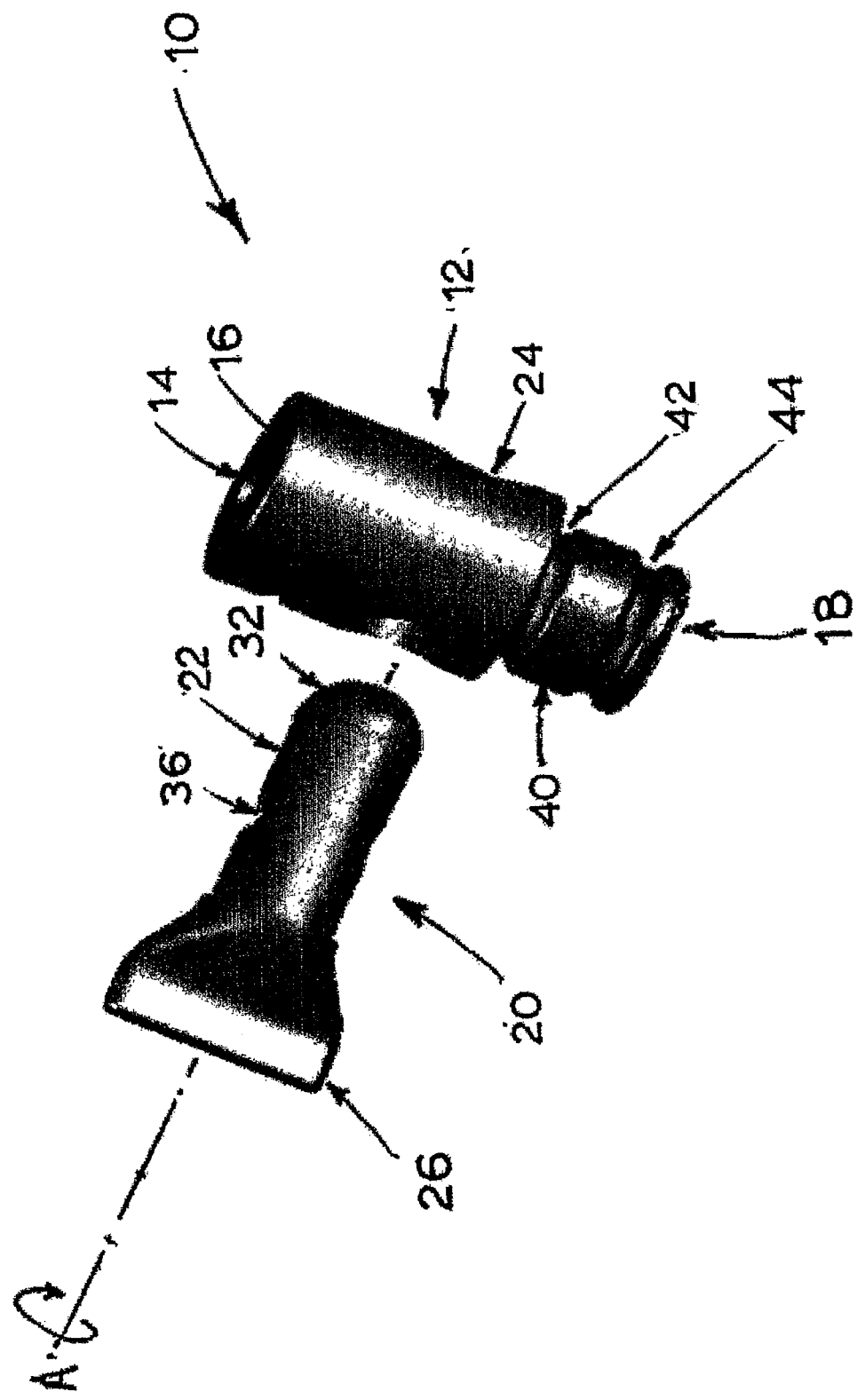
FIG. 1 shows an exploded perspective view of a device for use in stretching the foreskin of a subject.
Figure 2:
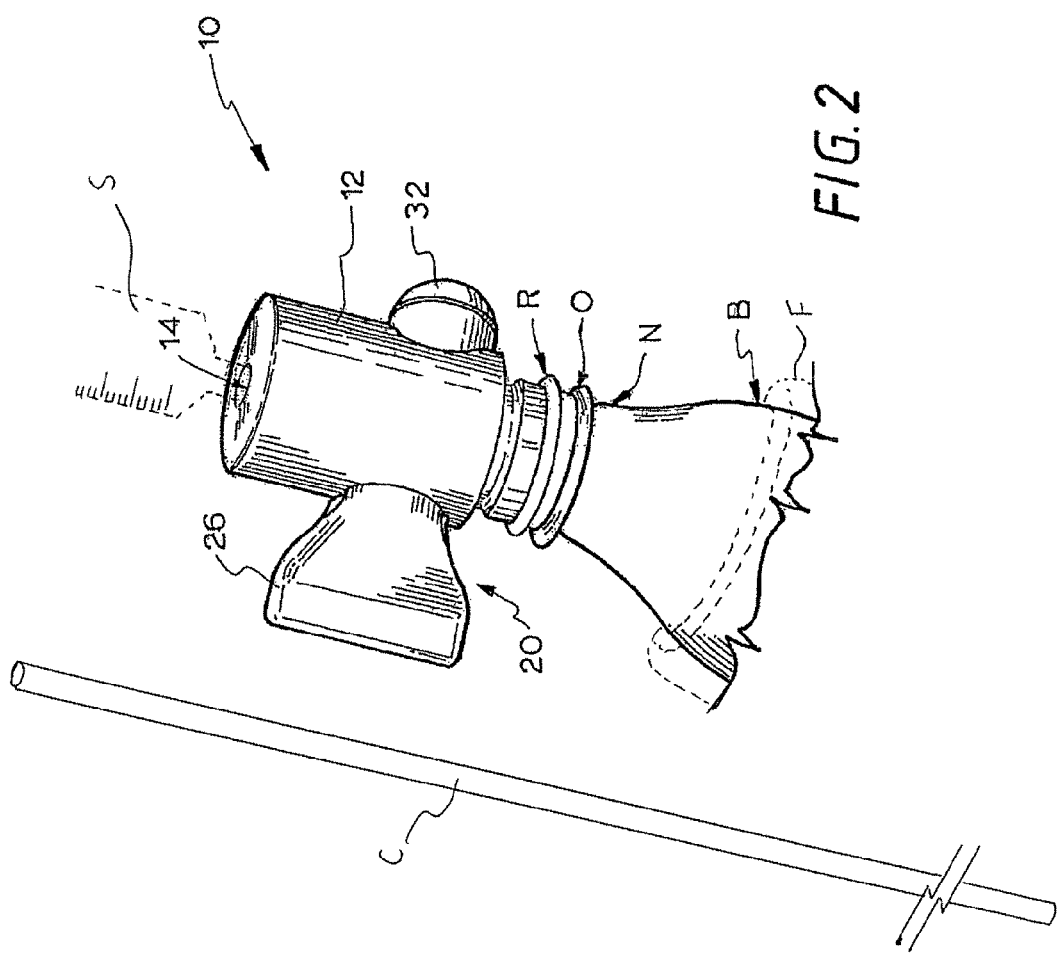
FIG. 2 shows an assembled perspective view of the device of FIG. 1 with a balloon neck clamped thereon.
Figure 3:
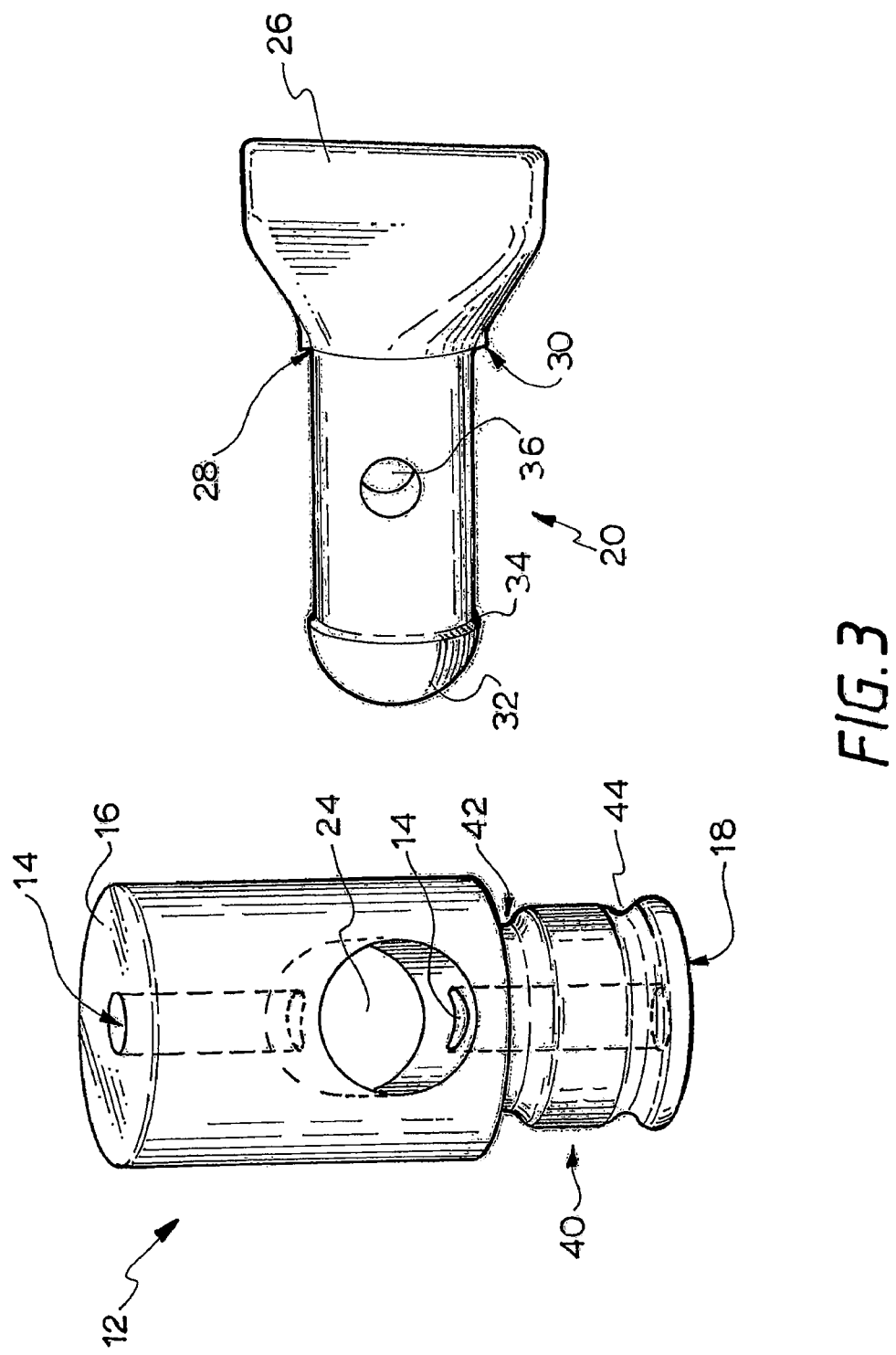
FIG. 3 shows a perspective schematic view of the device of FIG. 1 in more detail.

Referring to FIGS. 1 to 3, a gentle foreskin stretching (GFS) device 10 for use in stretching the foreskin of a subject comprises a body in the form of an elongate tube-like part 12. Part 12 has a passage in the form of a bore 14 that extends centrally therethrough, from a device proximal end 16 to a device distal end 18. At the proximal end the bore 14 is sized to snugly receive therein the nozzle of eg. a luer syringe. The use of a syringe makes for easy expansion (eg. inflation) and contraction (eg. deflation) of a balloon mounted to the GFS device.

The GFS device further comprises a fluid flow regulating member in the form of a tap 20. The tap can be positioned to extend transversely across the bore 14 to selectively close the device to fluid (eg. gas) flow therethrough. The tap enables the balloon to be maintained in an expanded (eg. inflated) state without requiring balloon twisting or a balloon clip, making the GFS device easy to use and also preserving balloon life.

The tap 20 is rotatable about its lengthwise axis A to respectively open and close the device bore 14 to fluid (eg. gas) flow therethrough. The tap has a shank 22 that is sized to be snugly received and rotatable within an aperture 24 that extends transversely right through the tube-like part 12, intersecting with the bore 14. A manually graspable enlarged tap head 26 is located at the shank proximal end 28, with this head being located outside the aperture for finger access when the tap is snugly received in the aperture (FIG. 2). The tap head 26 also defines a shoulder 30 at the shank proximal end 28 to delimit the extent of insertion of the tap in the aperture. The shank distal end has a slightly oversized hemispherical dome 32 that also defines a shoulder 34 thereat, the dome 32 adapted to deform as the tap is inserted through the aperture 24 and to snap back to reestablish shoulder 34 once the dome has passed through the aperture (FIG. 2), thereby locking the tap 20 in the part 12.

The tap has a transverse hole 36 extending therethrough that is of approximately the same diameter as the bore 14. By rotating the tap about its axis A the hole 36 can be selectively aligned with the bore 14 whereby fluid can flow through the GFS device via the bore 14 and hole 36. Again, by rotating the tap about its axis A to progressively misalign bore 14 and hole 36 such fluid flow is progressively restricted and is ultimately prevented (ie. device is closed). This prevention of fluid flow can be effected quickly, though in some cases it may be desirable to impart a restricted fluid flow through the GFS device to provide subtle adjustments to the balloon shape.

The tube-like part 12 is shaped at its distal end 18 to step down in diameter to define a spigot 40 at that end, over which the neck N of balloon B can be received, as shown in FIG. 2. This makes for easy balloon mounting to the GFS device so that a fluid (eg. gas) passed through the GFS device can cause the balloon to expand.

The spigot 40 comprises two adjacent and parallel circumferential grooves 42 and 44, each adapted for receiving an O-ring therein. One O-ring, or two respective O-rings for the grooves 42 and 44, can be used to easily and rapidly fasten the balloon neck N to the spigot (FIG. 2). Alternatively, one groove 42 can receive a peripheral end rib R of the balloon therein, and the other groove 44 can receive the O-ring.

EXAMPLE

Method for Stretching the Foreskin

In this example, the method comprised the following steps:
1. With the tap 20 in the open position, the balloon B was located on the spigot 40 of the GFS device 10 by an O-ring O.
2. The non-inflated balloon B was positioned within the foreskin F with the aid of an insertion rod. The insertion rod comprised a blunt (or round)-ended rod C of an effective diameter to pass right through the bore 14 and hole 36 and into the balloon.
3. The insertion rod C was then used to manipulate the balloon into position under the foreskin F. Once in place, the insertion rod was removed.
4. A luer syringe S was located in the bore distal end and air was ejected from the syringe S to be forced through the bore 14 and into the balloon, to inflate it to a desired level of inflation.
5. With the balloon in its desired expanded state, the tap 20 was rotated closed, to close (or seal) the GFS device to further air flow in or out of the device.
6. The balloon was maintained in its expanded state within the foreskin for a period of time of around 3-5 minutes (though the period was varied to be optimal such that, after use of the GFS device, a desired semi-permanent or permanent foreskin stretch was maintained in the human male user).
7. The tap was then opened to deflate the balloon and allow it to be removed from the foreskin.
8. Steps 1 to 7 are repeated daily for a period of 14 consecutive days.

Observations of the GFS Device and Method

The GFS device was observed to provide an alternative to circumcision by treating phimosis (tight foreskin) which is the inability to properly retract the foreskin.

Although the device was primarily designed to treat phimosis, it was noted that the device may be used to stretch the foreskin so as to enhance sexual functioning and to increase enjoyment of some sexual activities.

The device enabled the balloon once inserted through the opening in the foreskin to apply a gentle and even pressure against the skin of the foreskin to stretch the skin. When the GFS device was used every day for a couple of weeks it allowed a permanent or semi-permanent stretching of the foreskin.

The device had several advantages over existing devices. The GFS device was observed to be more robust and yet gentler than existing devices. The device was able to be made from just two molded plastic parts and so was able to be mass produced using injection or other molding processes such as die casting. Forming the tube-like body part 12 as a single (unitary) piece allowed complete fluid-tight sealing and minimized any damage caused to the balloon by multi-part devices. The body part 12 was also able to be formed with a constant lumen (bore 14) along its entire length with a diameter at the proximal end designed to fit a standard luer syringe. The tap with a lumen (hole 36) of the same diameter as the bore 14 allowed for easy and rapid opening and closing of the device.

Also, a huge variety of balloon shapes were able to be used with the device, for example, a balloon shape that is optimized to foreskin stretching. Also, different size balloons can be employed for users of different ages.

In one version the body part 12 was molded of silicon or another soft rubber and the tap was molded in a hard plastic, for example, a poly-aryl-ether-sulfone (such as marketed under the trade mark UDEL or Radel® R) or a poly-phenyl-sulfone (PPSU), or polycarbonate, or similar.

Whilst a number of embodiments have been described, it will be appreciated that the device and method can be embodied in many other forms.

For example, the GFS device is designed for and is typically employed on a human male, usually both adult and younger human males, or even on other mammals having a foreskin. It was noted in this regard that phimosis is more common in young males. In each case, the balloon used was sized accordingly.

In a further example, although a tap is a simple means of providing fluid flow regulation, other means can be employed such as a controllable (eg. switchable) valve located in the part 12 at bore 14, or a gate that is slidable in the part 12 to selectively occlude or open the bore 14, etc.

Also, whilst a gas such as air from a syringe is typically used to inflate/deflate the balloon, in some applications a liquid such as water may be employed to expand the balloon (eg. warm water in winter months). Other fluid injection devices such as a micro-pump could be used.

In yet a further example, the device can comprise a single disposable and/or re-useable unit with both the pump or syringe for the fluid, as well as the balloon, being permanently affixed to the body.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

The invention claimed is:

1. A method for stretching a foreskin of a subject, the method comprising the steps of:
   providing a device configured to stretch a foreskin of a subject, the device comprising a body including a passage, a balloon, and a fluid flow regulator;
   locating the balloon between the foreskin and glans, and then manipulating the balloon to be partly or wholly under the foreskin by contacting the balloon with a manipulation device;
   actuating the fluid flow regulator to open the passage to fluid flow;
   introducing a fluid through the passage and into the balloon to cause the balloon to expand so as to apply a gentle and even pressure against the foreskin to stretch the foreskin;
   whilst maintaining the balloon in an expanded state, actuating the fluid flow regulator to close the passage to fluid flow.

2. A method as claimed in claim 1, wherein the balloon is secured on a distal end of the body by locating at least one O-ring to extend around and clamp a neck of the balloon onto the distal end.

3. A method as claimed in claim 1, wherein the balloon is inflated by a gas.

4. A method as claimed in claim 3, wherein the gas is injected out of a syringe that has been inserted into a proximal end of the passage.

5. A method as claimed in claim 3, wherein the gas includes air.

6. A method as claimed in claim 1, wherein the balloon is maintained in the expanded state under the foreskin for a period of time.

7. A method as claimed in claim 1, wherein the balloon is manipulated under the foreskin by manipulating an inside surface of the balloon.

8. A method as claimed in claim 7, wherein the inside surface of the balloon is manipulated by the manipulation device which includes a rod that is insertable through the passage.

* * * * *